United States Patent
Kataoka et al.

(10) Patent No.: US 9,772,322 B2
(45) Date of Patent: Sep. 26, 2017

(54) CELL OBSERVATION DEVICE, AND CELL OBSERVATION METHOD

(71) Applicant: HAMAMATSU PHOTONICS K.K., Hamamatsu-shi, Shizuoka (JP)

(72) Inventors: Takuji Kataoka, Hamamatsu (JP); Taira Ito, Hamamatsu (JP); Natsumi Saito, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 228 days.

(21) Appl. No.: 14/438,055

(22) PCT Filed: Oct. 23, 2013

(86) PCT No.: PCT/JP2013/078716
§ 371 (c)(1),
(2) Date: Apr. 23, 2015

(87) PCT Pub. No.: WO2014/065329
PCT Pub. Date: May 1, 2014

(65) Prior Publication Data
US 2015/0276708 A1 Oct. 1, 2015

(30) Foreign Application Priority Data
Oct. 25, 2012 (JP) .................. 2012-235677

(51) Int. Cl.
*G01N 15/00* (2006.01)
*G01N 21/00* (2006.01)
(Continued)

(52) U.S. Cl.
CPC ..... *G01N 33/4836* (2013.01); *G01N 15/1031* (2013.01); *G01N 15/1431* (2013.01);
(Continued)

(58) Field of Classification Search
USPC .................. 356/445–448, 450–458
See application file for complete search history.

(56) References Cited

U.S. PATENT DOCUMENTS 5,364,521 A * 11/1994 Zimmermann .. G01N 27/44743
204/604
6,470,226 B1 * 10/2002 Olesen ............. G01N 33/48728
435/287.1
(Continued)

FOREIGN PATENT DOCUMENTS

JP 2001-188044 7/2001
JP 2004-147517 5/2004
(Continued)

OTHER PUBLICATIONS

H. Cheng et al., "Calcium Sparks: Elementary Events Underlying Excitation-Contraction Coupling in Heart Muscle", Science, vol. 262, No. 5134, Oct. 29, 1993, p. 740-p. 744, XP055272468.

*Primary Examiner* — Tri Ton
*Assistant Examiner* — Jarreas C Underwood
(74) *Attorney, Agent, or Firm* — Drinker Biddle & Reath LLP

(57) ABSTRACT

A cell observation system 1, for measuring fluorescence emitted from a cell held by a microplate 20 having a plurality of wells 21, comprises a microplate holder 11 for mounting the microplate 20, an electrical stimulator 16 arranged with a plurality of electrode pairs 17 including positive and negative electrodes 17b, 17a, a position controller 30 for controlling a position of the electrical stimulator 16 so as to place the electrode pairs 17 within the wells 21, a moving image acquisition unit 40 for detecting the fluorescence from the sample S within the wells 21, and a data analyzer 50 for setting a part of a region facing the positive electrode 17b on the well 21 as an analysis region and analyzing an optical intensity in the analysis region so as to acquire analysis information concerning the sample S.

13 Claims, 20 Drawing Sheets

(51) Int. Cl.
*G01N 33/48* (2006.01)
*G01N 33/483* (2006.01)
*G01N 21/64* (2006.01)
*G01N 15/14* (2006.01)
*G01N 15/10* (2006.01)

(52) U.S. Cl.
CPC ..... *G01N 15/1434* (2013.01); *G01N 15/1436* (2013.01); *G01N 15/1456* (2013.01); *G01N 15/1484* (2013.01); *G01N 21/6452* (2013.01); *G01N 2015/0065* (2013.01); *G01N 2015/1006* (2013.01)

(56) References Cited

U.S. PATENT DOCUMENTS

| | | | | |
|---|---|---|---|---|
| 6,783,649 | B2 * | 8/2004 | Hedberg | G01N 27/44782 204/451 |
| 7,539,362 | B2 * | 5/2009 | Teramura | G01J 3/4535 385/12 |
| 8,658,349 | B2 * | 2/2014 | Teich | B01L 3/5025 435/4 |
| 8,994,360 | B2 * | 3/2015 | Takeshita | C12M 41/36 324/71.4 |
| 9,079,189 | B2 * | 7/2015 | Garcia | B03C 5/005 |
| 9,091,151 | B2 * | 7/2015 | Jones | E21B 47/102 |
| 2006/0008906 | A1 * | 1/2006 | Wills | A61K 35/12 435/451 |
| 2011/0163744 | A1 * | 7/2011 | Nakayama | G01N 33/4833 324/249 |
| 2016/0299060 | A1 * | 10/2016 | Hokanson | G01N 21/31 |

FOREIGN PATENT DOCUMENTS

| | | |
|---|---|---|
| JP | 2005-514909 A | 5/2005 |
| JP | 2007-534927 A | 11/2007 |
| WO | WO 02/08748 | 1/2002 |
| WO | WO 03/006103 | 1/2003 |
| WO | WO 2010/027446 | 3/2010 |
| WO | WO-2011/132586 A1 | 10/2011 |

* cited by examiner

Fig.8
(a)
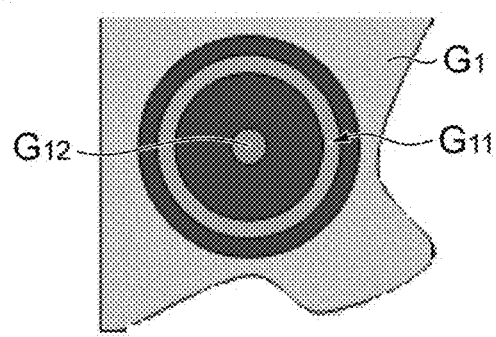
(b)
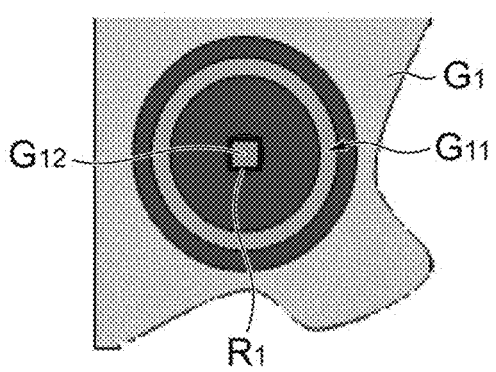

Fig.10
(a)
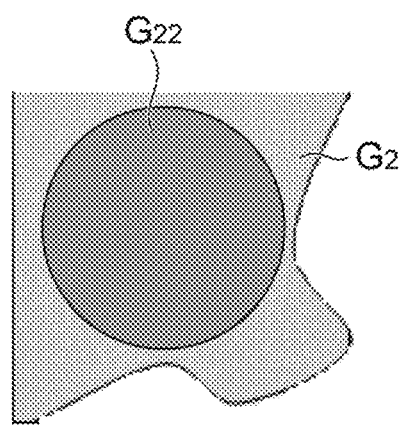
(b)
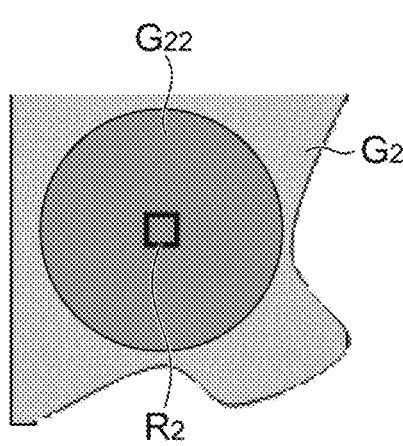

Fig.17
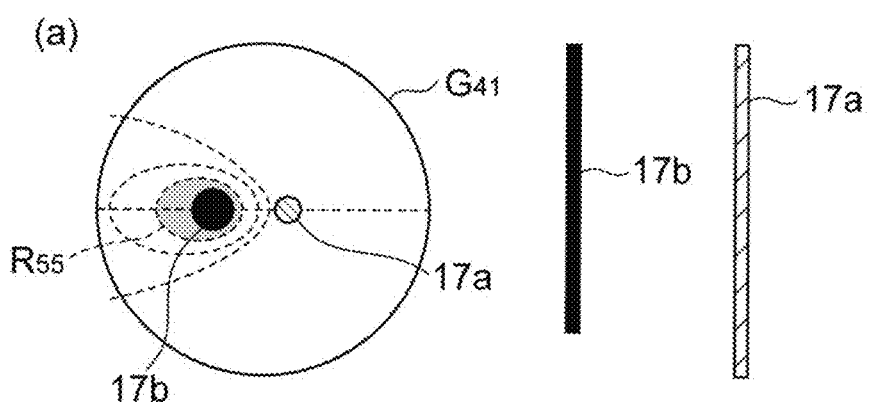
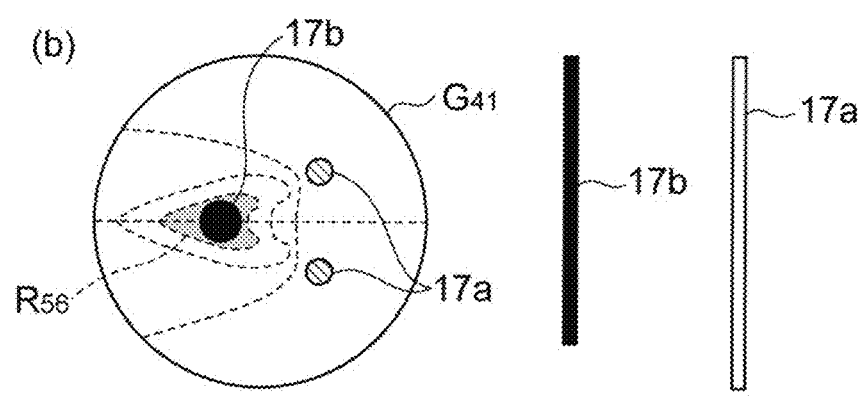

CELL OBSERVATION DEVICE, AND CELL OBSERVATION METHOD

TECHNICAL FIELD

The present invention relates to a cell observation system and a cell observation method which measure light emitted from a sample including a cell when a voltage is applied thereto.

BACKGROUND ART

In the field of drug discovery, there are cases where influences of drugs administered to samples such as cells are evaluated by measuring light emitted from the cells. Patent Literature 1 discloses a measurement device comprising an electrode array for generating an electric field in an observation region within a well for a multiwell plate in which a plurality of wells for placing cells therein are arranged. The electrode array is constituted by negative and positive electrodes which are two parallel plate electrodes. Patent Literature 2 discloses a measurement device which monitors a biological response to electric field stimulation of a cell by detecting fluorescence, while this measurement device employs a structure which can place an electrode pair in the form of a coaxial cable constituted by positive and negative electrodes in a well arranged with a cell.

CITATION LIST

Patent Literature

Patent Literature 1: Japanese Translated International Application Laid-Open No. 2007-534927
Patent Literature 2: Japanese Translated International Application Laid-Open No. 2005-514909

SUMMARY OF INVENTION

Technical Problem

In the measurement device disclosed in the above-mentioned Patent Literature 1, however, the observation region within a well arranged with a cell is a circular region in the middle between the negative and positive electrodes. Hence, a region less reactive to the electric field stimulation may also be subjected to observation, whereby highly sensitive evaluation results may not be obtained. On the other hand, the measurement device disclosed in the above-mentioned Patent Literature 2 does not set observation regions within wells in particular.

In view of such problems, it is an object of the present invention to provide a cell observation system and cell observation method which can highly sensitively analyze light from samples in a plurality of arranged holding units.

Solution to Problem

For achieving the above-mentioned problems, the cell observation system of the present invention is a cell observation system for measuring light emitted from a cell held by a sample case having a plurality of holding units arranged therein for holding a sample including the cell; the cell observation system comprising a mounting unit for mounting the sample case, an electrical stimulator arranged with a plurality of electrode pairs including positive and negative electrodes, a position control unit for controlling a position of the electrical stimulator so as to place the electrode pairs within the holding units of the sample case, a light detection unit for detecting the light from the sample within the holding units of the sample case, and an information analysis unit for setting a part of a region facing the positive electrode on the holding unit as an analysis region for an optical intensity distribution obtained according to a result of detection by the light detection unit and analyzing an optical intensity in the analysis region so as to acquire analysis information concerning the sample.

The cell observation method of the present invention is a cell observation method for measuring light emitted from a cell held by a sample case having a plurality of holding units arranged therein for holding a sample including the cell; the method comprising a mounting step of mounting the sample case on a mounting unit, a position control step of controlling a position of an electrical stimulator arranged with a plurality of electrode pairs including positive and negative electrodes so as to place the electrode pairs within the holding units of the sample case, a light detection step of detecting the light from the sample within the holding units of the sample case, and an information analysis step of setting a part of a region facing the positive electrode on the holding unit as an analysis region for an optical intensity distribution obtained according to a result of detection in the light detection step and analyzing an optical intensity in the analysis region so as to acquire analysis information concerning the sample.

In the foregoing cell observation system and cell observation method, electrode pairs including positive and negative electrodes are placed within a plurality of holding units arranged in a sample case, light from a sample within the holding units is detected by a light detection unit in a state where an electric field is generated by the electrode pairs, for an optical intensity distribution according to a result of the detection an information analysis unit sets a part of a region facing the positive electrode on the holding unit as an analysis region, and analysis information is acquired according to an optical intensity of the analysis region. Hence, a range including the cell having generated a reaction to electrical stimulation is analyzed efficiently, whereby the ratio of the optical intensity caused by the reaction of the cell to the optical intensity caused by noise can be increased. As a result, light from a sample including a cell can be analyzed highly sensitively.

Advantageous Effects of Invention

The present invention makes it possible to highly sensitively analyze light from samples in a plurality of arranged holding units.

BRIEF DESCRIPTION OF DRAWINGS

FIG. 8 is a diagram illustrating a two-dimensional optical image $G_1$ including a reflected image of an electrode pair 17 acquired by a data analyzer 50 at the time of the operation for determining an analysis region;

FIG. 10 is a diagram illustrating a two-dimensional optical image $G_1$ including a reflected image of the electrode pair 17 acquired by a data analyzer 50 at the time of the operation for determining an analysis region;

FIG. 17 is a diagram illustrating structures of electrode pairs 17 in accordance with modified examples of the embodiment and images of analysis regions set correspondingly thereto by the data analyzer 50;

DESCRIPTION OF EMBODIMENTS

Figure 1:
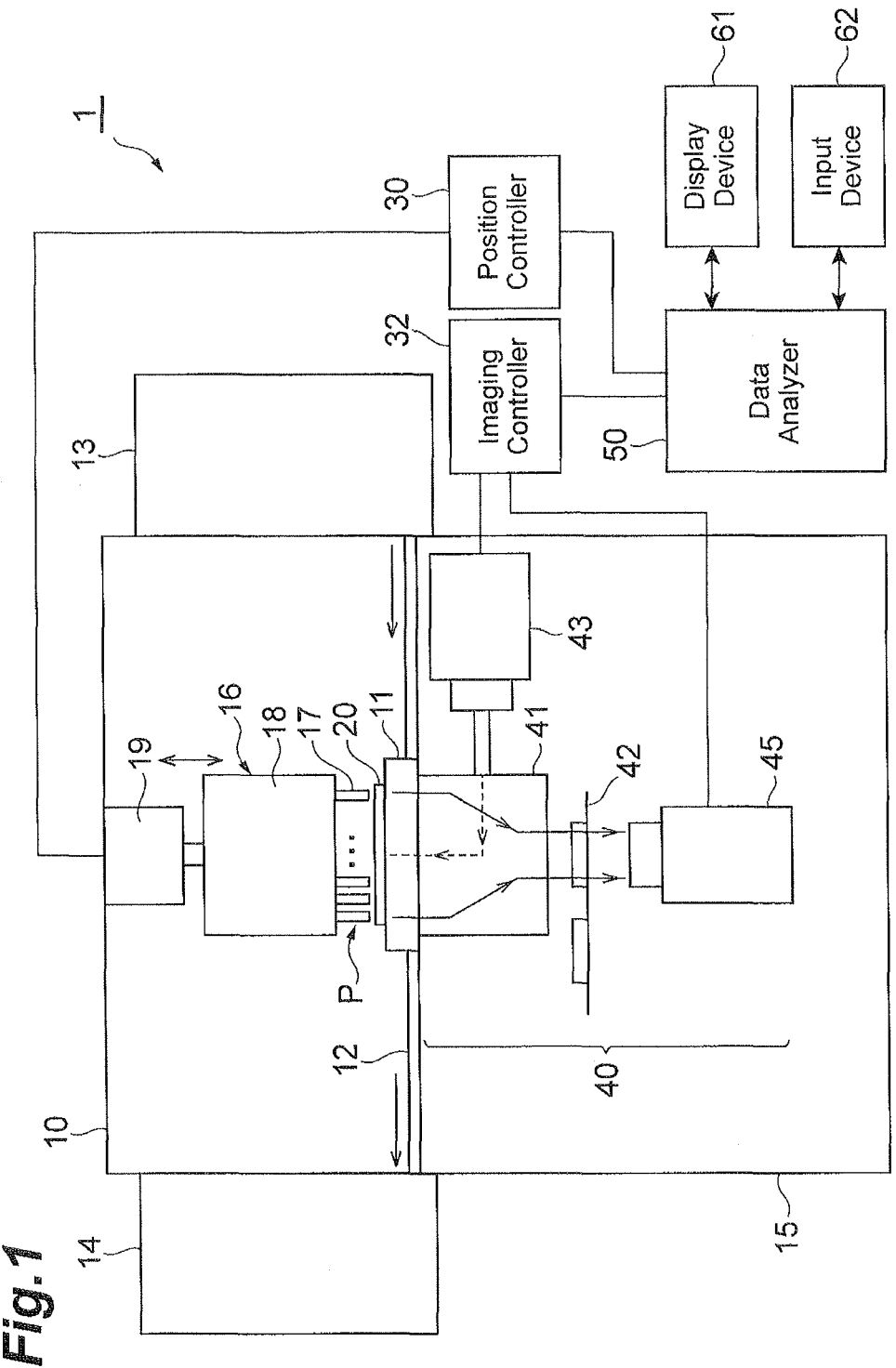
FIG. 1 is a diagram illustrating a schematic structure of a cell observation system 1 in accordance with a preferred embodiment of the present invention.

In the following, embodiments of the cell observation system and cell observation method in accordance with the present invention will be explained in detail with reference to the accompanying drawings. In the explanation of drawings, the same constituents will be referred to with the same signs while omitting their overlapping descriptions. The drawings are made for explanation and emphasize parts to be explained in particular. Therefore, members in the drawings are not always to scale.

Figure 2:
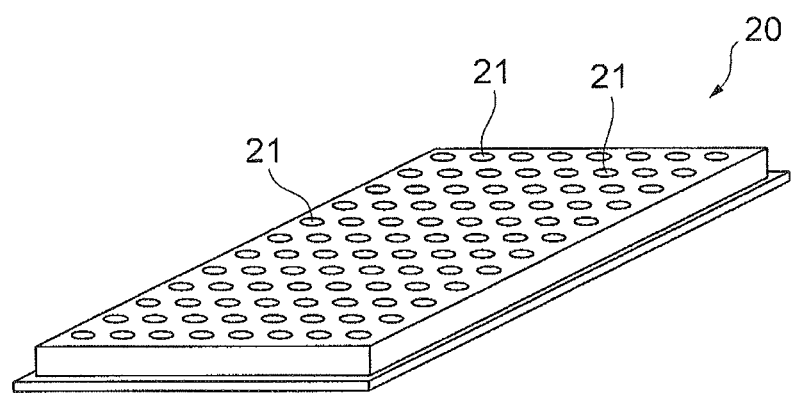
FIG. 2 is a perspective view illustrating a structure of a microplate 20 in FIG. 1.
Figure 3:
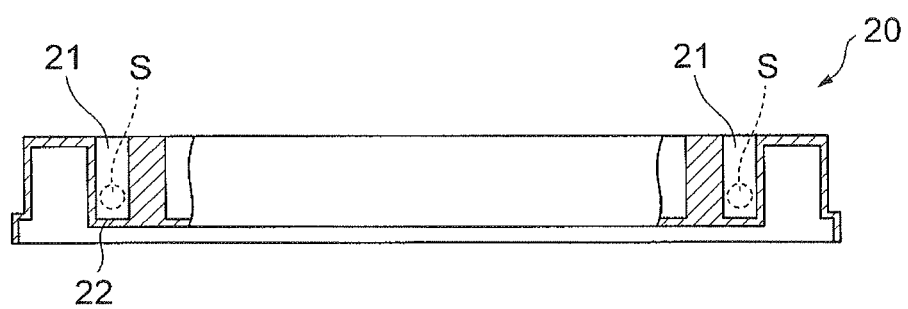
FIG. 3 is a side sectional view illustrating a cross-sectional structure of the microplate 20 in FIG. 1.

FIG. 1 is a structural diagram schematically illustrating an embodiment of a cell observation system 1 in accordance with the present invention. FIG. 2 is a perspective view illustrating an example of the structure of a microplate 20. FIG. 3 is a side sectional view illustrating a cross-sectional structure of the microplate 20 in FIG. 2. The cell observation system 1 in accordance with this embodiment is a device, which uses the microplate 20 as a sample case, for measuring fluorescence from a sample S placed at a measurement position P while being held by the microplate 20.

The sample S includes a predetermined cell. An example of the predetermined cell is a neuron. The cell observation system and cell observation method in this embodiment are employable not only for fluorescence measurement, but also for light measurement for measuring light in general, such as phosphorescence and luminescence, for example, emitted from samples. In the following, the structure of the cell observation system 1 will be explained.

The cell observation system 1 illustrated in FIG. 1 comprises a data acquisition device 10, a position controller (position control unit) 30, an imaging controller 32, and a data analyzer (information analysis unit) 50. The data acquisition device 10 has a dark box 15 for containing therewithin the microplate 20 holding a cell subjected to fluorescence measurement and a moving image acquisition unit 40 which is installed within the dark box 15 and used for measuring fluorescence from the sample S placed at the measurement position P.

As illustrated in FIGS. 2 and 3, the microplate 20 used as the sample case in this embodiment is a planar member in which a plurality of wells (holding units) 21 are arranged in a two-dimensional array, which is constructed such that the sample S can be held in each of the plurality of wells 21. Examples of cross-sectional forms of the wells 21 include circles, ellipses, and rectangles. In the structural example illustrated in FIG. 2, 8×12=96 circular wells 21 are arranged in a two-dimensional array as a plurality of wells 21. The microplate 20 has a bottom face 22 formed from a material which can transmit therethrough excitation light, with which the sample S is irradiated for fluorescence measurement, and fluorescence emitted from the sample S. In general, it is sufficient for the bottom face 22 of the microplate 20 in the cell observation system 1 to be formed from a material which can transmit therethrough light emitted from the sample S to be measured.

Within the dark box 15, the microplate 20 is mounted on a microplate holder (mounting unit) 11 having an opening for observing fluorescence. A microplate transfer mechanism 12 for transferring the microplate 20 and microplate holder 11 in a predetermined direction (from the right side to the left side in FIG. 1) within the dark box 15 is also installed within the dark box 15.

Installed on one side serving as the inlet side of the dark box 15 in the transfer direction of the microplate 20 in the transfer mechanism 12 is an inlet microplate stocker 13 for stocking a predetermined number of (e.g., 25) microplates 20 holding the sample S before measurement. Installed on the other side serving as the outlet side of the dark box 15 in the transfer direction of the microplate 20 is an outlet microplate stocker 14 for stocking the microplates 20 after measurement.

In this structure, the microplate 20 taken from the inlet microplate stocker 13 into the dark box 15 is held by the microplate holder 11 and transferred by the transfer mechanism 12. The microplate 20 is once stopped at the measurement position P, and light measurement necessary for the sample S held by the microplate 20 is performed in this state. After the measurement is completed, the microplate 20 is transferred by the transfer mechanism 12 again, so as to be taken out to the outlet microplate stocker 14. In FIG. 1, specific structures for taking in, transferring, and taking out the microplate 20 are not depicted for the transfer mechanism 12 and stockers 13, 14.

Installed above the measurement position P where the microplate 20 and sample S are placed at the time of performing fluorescence measurement is an electrical stimulator 16 to be inserted into the wells 21 of the microplate 20 in order to generate an electric field in the sample S. Installed under the measurement position P is the moving image acquisition unit (light detection unit) 40 used for detecting fluorescence emitted through the bottom face 22 of the microplate 20 from the sample S contained within the wells 21.

The moving image acquisition unit 40 is a moving image acquisition means which detects a two-dimensional optical image representing a two-dimensional optical intensity distribution of the microplate 20 including light emitted from the sample S held within the wells 21 of the microplate 20 and acquires moving image data of the two-dimensional optical image. The two-dimensional optical image to be detected may be an optical intensity distribution including light emitted from the sample S held within at least one well 21. The moving image acquisition unit 40 is constituted by an imaging device 45, a light-guiding optical system 41, an optical filter unit 42, and an excitation light source 43. The imaging device 45 has a two-dimensional pixel structure in which a plurality of pixels are arranged two-dimensionally and detects a fluorescence image which is a two-dimensional light detection image caused by the fluorescence emitted from the sample S. As the imaging device 45, a highly sensitive CCD camera or CMOS imaging camera can be used, for example. If necessary, an image intensifier, a relay lens, and the like may be placed in front of the camera, so as to construct the moving image acquisition unit 40. The moving image acquisition unit 40, which may acquire still images, has a function as an image acquisition unit for acquiring a moving image and/or a still image.

The light-guiding optical system 41 is installed between the measurement position P where the microplate 20 is placed and the imaging device 45. The light-guiding optical system 41 is an optical system which guides to the imaging device 45 a two-dimensional optical image of the microplate 20 holding the sample S in each of the plurality of wells 21 as seen from the bottom face 22 side. A specific structure of the light-guiding optical system 41 may be constructed as appropriate by optical elements which can achieve necessary functions (e.g., condensing function and optical image reducing function) according to the structures of the microplate 20 and imaging device 45 and the like. An example of such optical elements is a tapered fiber (see Japanese Patent Application Laid-Open No. 2001-188044). The light-guiding optical system 41 may also be constructed such as to use a light irradiation device having a light-guiding member having irregularities (see Japanese Patent Application Laid-Open Nos. 2010-230397 and 2010-230396).

In FIG. 1, the optical filter unit 42 adapted to place an optical filter onto the light-guiding path for fluorescence, switch it, and so forth when necessary is further installed between the light-guiding optical system 41 and imaging device 45. However, the optical filter unit 42 may be omitted when unnecessary.

The excitation light source 43 is an excitation light supply means for supplying the sample S with excitation light for fluorescence measurement. A specific structure of the excitation light source 43, an example of which is constituted by an illumination light source for supplying light and an optical filter unit for selecting or switching a wavelength of the excitation light, may be constructed as appropriate according to the kind of the sample S subjected to fluorescence measurement, the wavelength of the excitation light irradiating the sample S, and the like. The excitation light source 43 may be omitted when no supply of excitation light is necessary according to the kind of light measurement performed for the sample S.

In this embodiment, the light-guiding optical system 41 is constructed as an optical system which can guide the two-dimensional optical image from the microplate 20 and sample S to the imaging device 45 and the excitation light from the excitation light source 43 to the sample S. For example, such an optical system can be constructed by using a dichroic mirror which transmits therethrough the fluorescence from the microplate 20 and reflects the excitation light from the excitation light source 43. FIG. 1 schematically illustrates optical paths of the fluorescence and excitation light in the light-guiding optical system 41 with solid and broken lines, respectively.

Figure 4:
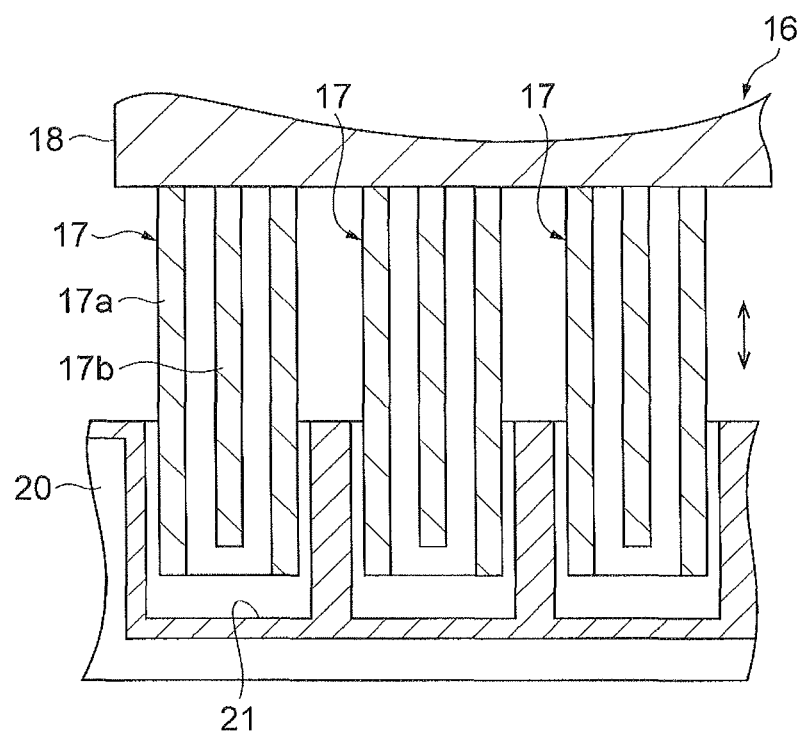
FIG. 4 is a partially broken sectional view of an electrical stimulator 16 in FIG. 1.

The structure of the electrical stimulator 16 will now be explained in detail. FIG. 4 is a partially broken sectional view of the electrical stimulator 16 in a state inserted in the microplate 20. The electrical stimulator 16 has a structure in which a plurality of electrode pairs 17 extending vertically toward the microplate 20 are secured to a base part 18 so as to be arranged two-dimensionally. Specifically, the electrode pairs 17 are arranged two-dimensionally so as to correspond to the two dimensional array arrangement of the plurality of wells 21 of the microplate 20 and extend while facing the wells 21 of the microplate 20. Each electrode pair 17 is constituted by a negative electrode 17a having a cylindrical form with an open leading end and a rod-shaped (e.g., columnar) positive electrode 17b inserted into the negative electrode 17a so as to be placed on the center axis of the negative electrode 17a, while the negative electrode 17a has an outer diameter smaller than the inner diameter of the well 21. The cylindrical form of the negative electrode 17a may have either a circular or elliptical cross section. The electrode pair 17 also has such a structure that the leading end of the positive electrode 17b is retracted by a predetermined distance (e.g., within the range of at least 1 μm but not more than 1.0 mm) from the opening surface on the leading end of the negative electrode 17a, i.e., such a form that the distance from the base part 18 to the leading end of the positive electrode 17b is shorter by the predetermined distance than the distance from the base part 18 to the leading end of the negative electrode 17a. This forms a structure in which the rod-shaped positive electrode 17b is contained within the negative electrode 17a in the cylindrical form, the positive electrode 17b does not project from the leading end of the negative electrode 17a, and the leading end of the negative electrode 17a and that of the positive electrode 17b are not flush with each other. The electrode pair 17 is not limited to one in which each of the negative and positive electrodes 17a, 17b is constituted by one member, but one or both of them may be constituted by a plurality of members.

The electrical stimulator 16 is also provided with a shifter mechanism 19 for supporting the electrode pairs 17 with the base part 18 interposed therebetween. The shifter mechanism 19, which is a driving mechanism for moving the electrode pairs 17 toward or away from the microplate 20, drives the electrode pairs 17 so as to place them into their opposing wells 21 when observing the sample S and separate them from within the wells 21 when the observation of the sample S is completed.

Coupled to thus constructed data acquisition device 10 are the position controller (position control unit) 30 and imaging controller 32. The position controller 30 is electrically coupled to the shifter mechanism 19 and controls the shifter mechanism 19 such that the electrode pairs 17 are placed within the wells 21 of the microplate 20 when starting light measurement of the sample S. The position controller 30 is also electrically coupled to the electrode pairs 17 so as to apply predetermined voltages to the negative and positive electrodes 17a, 17b, respectively, such that a predetermined potential difference occurs between the negative and positive electrodes 17a, 17b of the electrode pairs 17. The imaging controller 32 controls the irradiation with the excitation light by the excitation light source 43 and the capture of the two-dimensional fluorescence image in the microplate 20 by the imaging device 45.

The data analyzer 50 is further coupled to the position controller 30 and imaging controller 32. The data analyzer 50 is an analysis processing means which obtains through the imaging controller 32 the moving image data including the light detection image acquired by the moving image acquisition unit 40 and performs analysis processing for the moving image data. The data analyzer 50 also controls the fluorescence measurement for the sample S in the cell observation system 1 by regulating operations of individual parts of the data acquisition device 10 through the position controller 30 and imaging controller 32 (as will be explained later in detail). In FIG. 1, a display device 61 for displaying measurement results and the like and an input device 62 used for inputting data and instructions required for fluorescence measurement are coupled to the data analyzer 50.

Figure 5:
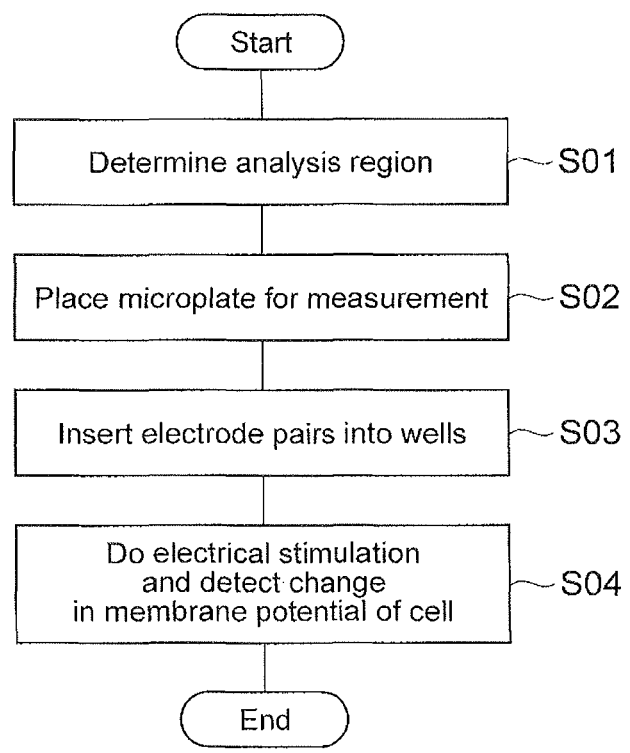
FIG. 5 is a flowchart illustrating operations of the cell observation system 1 at the time of measuring light from a sample S.
Figure 6:
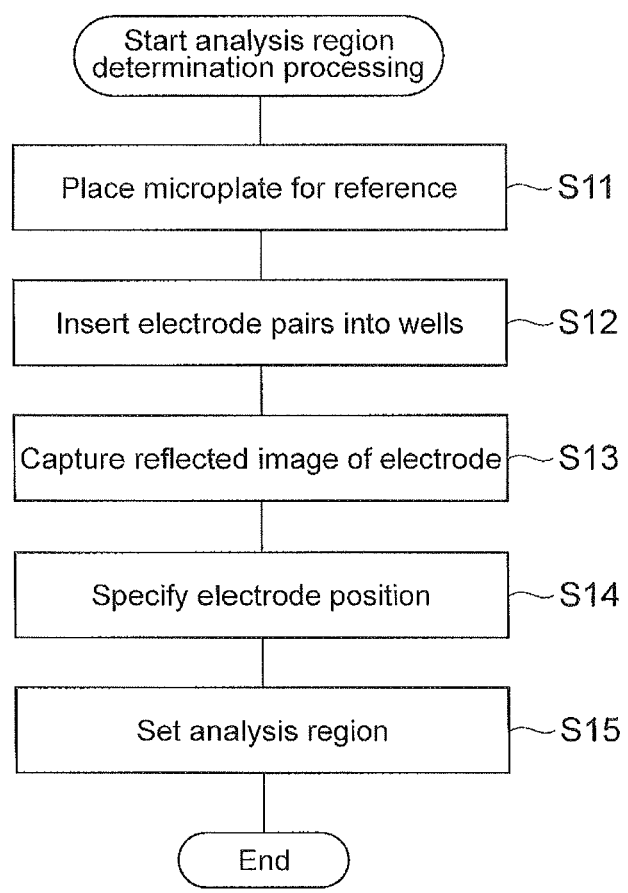
FIG. 6 is a flowchart illustrating details of the operation for determining an analysis region in FIG. 5.

With reference to FIGS. 5 and 6, the cell observation method in accordance with this embodiment will now be set forth in detail while explaining operations by the cell observation system 1 at the time of measuring light from the sample S. FIG. 5 is a flowchart illustrating operations of the cell observation system 1 at the time of measuring light from the sample S, while FIG. 6 is a flowchart illustrating details of the operation for determining an analysis region in FIG. 5.

First, a trigger to start light measurement of a cell is inputted through the input device 62, whereupon the data analyzer 50 determines an analysis region in a two-dimensional optical image included in the moving image data to be processed or still image (step S01: analysis region determination step). Subsequently, while being mounted on the microplate holder 11, the microplate 20 to be measured holding the sample S within the microplate stocker 13 is transferred by the microplate transfer mechanism 12 to the measurement position P within the dark box 15 (step S02: mounting step). Then, the data analyzer 50 controls the position of the electrical stimulator 16 by utilizing the shifter mechanism 19, so as to insert the leading ends of a plurality of electrode pairs 17 into their corresponding wells 21 of the microplate 20 (step S03: position control step). At this time, the electrode pairs 17 are inserted into the wells 21 until the leading ends of the negative electrodes 17a approach the bottom faces of the wells 21 by a predetermined distance. This places the positive electrodes 17b in a state where their leading ends are separated from the bottom faces of the wells 21 by about a predetermined distance (e.g., 1 µm to 1.0 mm).

Thereafter, the data analyzer 50 controls the position controller 30, so as to supply a voltage to the electrode pairs 17, thereby generating an electric field within the wells 21 of the microplate 20 (provision of electrical stimulation). In the state where the electric field is generated, the moving image acquisition unit 40 detects a two-dimensional optical image of the microplate 20 including fluorescence emitted from the sample S held within the wells 21, whereby the data analyzer 50 acquires moving image data representing the two-dimensional optical image. The moving image acquisition unit 40 has a frame rate which is set higher than the frequency at which the voltage is applied. For the two-dimensional optical image included in the acquired moving image data, the data analyzer 50 analyzes the optical intensity in an analysis region which is set in a part of a region facing the electrode pairs 17 of the microplate 20 on the microplate holder 11, whereby analysis information concerning the sample S is obtained and outputted to the display device 61 (step S04: light detection step and information analysis step). Since the cell in the sample S is provided with a membrane potential-sensitive fluorescent dye, a change in the membrane potential accompanying opening/closing of an ion channel of the cell is seen as a change in intensity of fluorescence when electrical stimulation is applied thereto. As techniques for analyzing optical intensity in such an analysis region, those calculating the amplitude of change, ratio of change, peak period, number of peaks, peak time, rise time, fall time, peak fluctuation range, and the like in pixel values in the analysis region as evaluation values may be considered.

Figure 7:
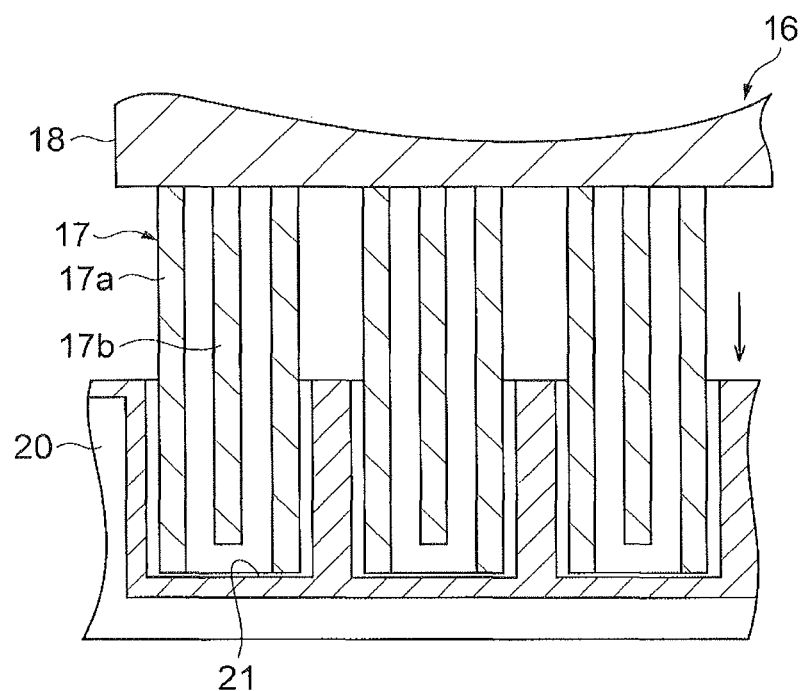
FIG. 7 is a partially broken sectional view illustrating a positional relationship between the electrical stimulator 16 and microplate 20 at the time of the operation for determining an analysis region.

Referring now to FIG. 6, the procedure of the analysis region determination step at the step S01 in FIG. 5 will be explained in detail. First, while being mounted on the microplate holder 11, a microplate 20 for reference having empty wells 21 within the microplate stocker 13 is transferred by the microplate transfer mechanism 12 to the measurement position P within the dark box 15 (step S11). Subsequently, the data analyzer 50 controls the position of the electrical stimulator 16, whereby the leading ends of a plurality of electrode pairs 17 are inserted into their corresponding wells 21 of the microplate 20 (step S12). FIG. 7 illustrates a positional relationship between the electrical stimulator 16 and microplate 20 at this time; the electrode pairs 17 are inserted into the wells 21 until the leading ends of the negative electrodes 17a approach the bottom faces of the wells 21 by a predetermined distance. This places the positive electrodes 17b in a state where their leading ends are separated from the bottom faces of the wells 21 by a predetermined distance (e.g., 1 µm to 1.0 mm).

Thereafter, while the excitation light source 43 irradiates the bottom face 22 of the microplate 20 (FIG. 3) with illumination light, the moving image acquisition unit 40 detects a two-dimensional optical image of the microplate 20 including a plurality of wells 21, and the data analyzer 50 acquires moving image data or still image data representing the two-dimensional optical image (step S13). Reflected images of the electrode pairs 17 are also projected on the two-dimensional image as a matter of course. For the two-dimensional optical image included in the acquired moving image data, the data analyzer 50 specifies and stores the positions of leading ends of the positive and negative electrodes 17b, 17a of the electrode pairs 17 (step S14). FIG. 8(a) illustrates an example of the two-dimensional optical image $G_1$ including a reflected image of the electrode pair 17 acquired by the data analyzer 50. As depicted, a ring-shaped reflected image $G_{11}$ of an end part of the negative electrode 17a and a circular reflected image $G_{12}$ of the positive electrode 17b are also projected on the two-dimensional optical image $G_1$. By detecting a difference in luminance, the data analyzer 50 specifies a range of the circular reflected image $G_{12}$ of the positive electrode 17b as a region where the leading end of the positive electrode 17b is extended onto the bottom face of the well 21.

The data analyzer 50 sets and stores a region including the specified range of the reflected image $G_{12}$ as an analysis region in the two-dimensional optical image (step S15). FIG. 8(b) illustrates an example of the analysis region set by the data analyzer 50 on the two-dimensional optical image $G_1$. As depicted, a rectangular analysis region $R_1$ including the circular reflected image $G_{12}$ of the positive electrode 17b is set on the two-dimensional optical image $G_1$. The form of the analysis region $R_1$ is not limited to rectangles, but may be any of other forms such as circles and polygons. Thus storing the position, coordinates, or range of the analysis region for each well 21 makes it unnecessary to set the analysis region each time mounting the microplate 20 on the microplate holder 11 when using the same kind of microplates at the time of light measurement, whereby the light measurement time can be shortened.

Figure 9:
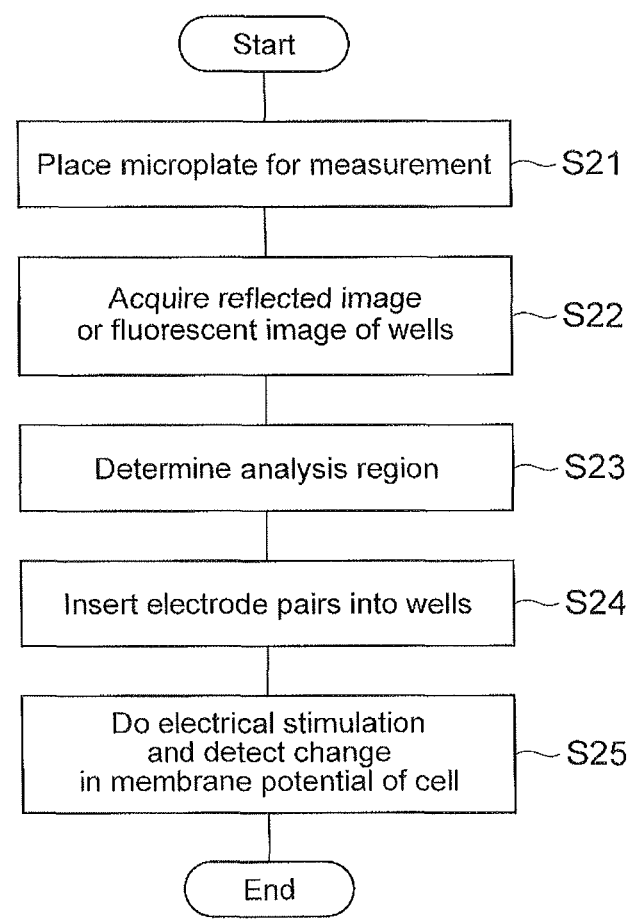
FIG. 9 is a flowchart illustrating another operation of the cell observation system 1 in FIG. 1 at the time of measuring light from the sample S.

The cell observation system 1 may set the analysis region in the middle of the light measurement operation for the sample S. In this case, the analysis region is set for each microplate used for measurement and thus can be configured accurately. FIG. 9 illustrates an operation procedure of the cell observation system 1 at the time of measuring light from the sample S in such a case.

First in this case, a trigger to start light measurement of a cell is inputted through the input device 62, whereupon the microplate 20 to be measured holding the sample S within the microplate stocker 13 is transferred by the microplate transfer mechanism 12 to the measurement position P within the dark box 15 while being mounted on the microplate holder 11 (step S21: mounting step). Subsequently, while the excitation light source 43 irradiates the bottom face 22 of the microplate 20 (FIG. 3) with illumination light, the moving image acquisition unit 40 detects a two-dimensional optical image of the microplate 20 including 96 wells 21, and the data analyzer 50 acquires moving image data representing the two-dimensional optical image (step S22). Also projected on the two-dimensional optical image are reflected images of the wells 21 and, in some cases, a fluorescence image emitted from the sample S. Further, for the two-dimensional optical image included in the acquired moving image data, the data analyzer 50 specifies a boundary position of the well 21 and determines an analysis region according to the boundary position (step S23). FIG. 10(a) illustrates an example of a two-dimensional optical image $G_2$ including a reflected image of the well 21 acquired by the data analyzer 50. As depicted, a circular reflected image $G_{22}$ of the well 21 is projected on the two-dimensional optical image $G_2$. By detecting a difference in luminance, the data analyzer 50 specifies a boundary of the circular reflected image $G_{22}$ of the well 21. Then, as illustrated in FIG. 10(b), the data analyzer 50 sets a rectangular analysis region $R_2$ at the center of the boundary of the reflected image $G_{22}$ in the two-dimensional optical image $G_2$. A rectangular region having a predetermined pixel width including a center point within the boundary of the reflected image $G_{22}$ is set as the analysis region $R_2$, while the pixel width of the analysis region $R_2$ is set beforehand to a value sufficient for the analysis region $R_2$ to include a region where the leading end of the positive electrode 17b is extended onto the bottom face of the well 21. The form of the analysis region $R_2$ is not limited to rectangles, but may be any of other forms such as circles and polygons.

Thereafter, the data analyzer 50 controls the position of the electrical stimulator 16 by utilizing the shifter mechanism 19, so as to insert the leading ends of a plurality of electrode pairs 17 into their corresponding wells 21 of the microplate 20 (step S24: position control step). Next, the data analyzer 50 controls the position controller 30, so as to supply a voltage to the electrode pairs 17, thereby generating an electric field within the wells 21 of the microplate 20 (provision of electrical stimulation). In the state where the electric field is generated, the moving image acquisition unit 40 detects a two-dimensional optical image of the microplate 20 including fluorescence emitted from the sample S held within the wells 21, whereby the data analyzer 50 acquires moving image data or still image data representing the two-dimensional optical image. For the two-dimensional optical image included in the acquired moving image data, the data analyzer 50 analyzes the optical intensity in an analysis region which is set in a part of a region facing the electrode pairs 17 of the microplate 20 on the microplate holder 11, whereby analysis information concerning the sample S is obtained and outputted to the display device 61 (step S25: light detection step and information analysis step).

Figure 11:
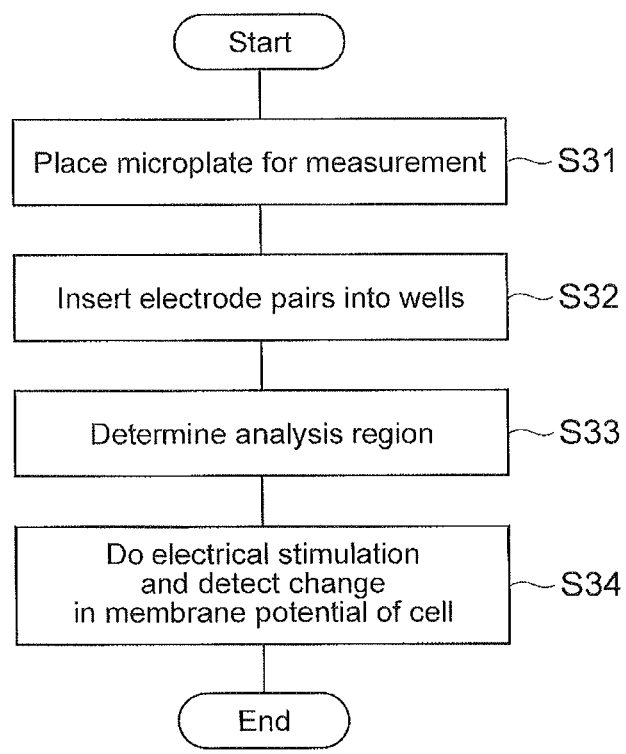
FIG. 11 is a flowchart illustrating another operation of the cell observation system 1 in FIG. 1 at the time of measuring light from the sample S.
Figure 12:
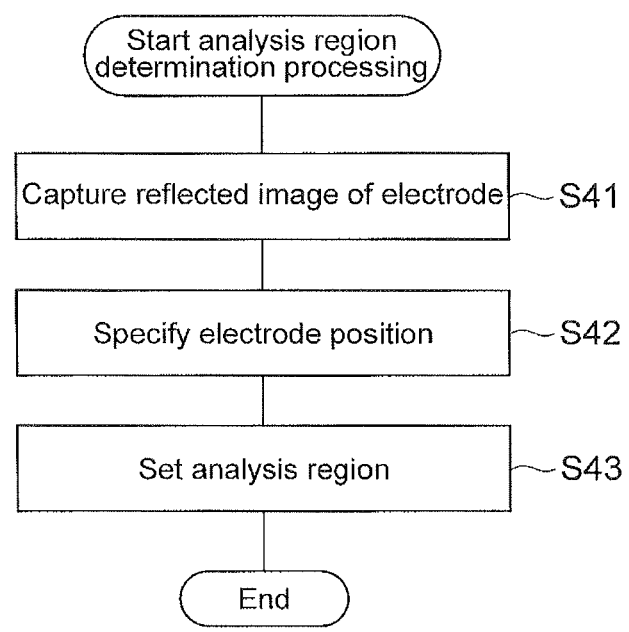
FIG. 12 is a flowchart illustrating details of the operation for determining an analysis region in FIG. 11.

The above-mentioned setting of the analysis region by the cell observation system 1 may be performed with reference to reflected images of the electrode pairs 17 appearing in the two-dimensional optical image of the microplate 20. FIGS. 11 and 12 illustrate an operation procedure of the cell observation system 1 at the time of measuring light from the sample S in such a case.

First in this case, the microplate 20 to be measured holding the sample S within the microplate stocker 13 is transferred by the microplate transfer mechanism 12 to the measurement position P within the dark box 15 while being mounted on the microplate holder 11 (step S31: mounting step). Subsequently, the data analyzer 50 controls the position of the electrical stimulator 16 by utilizing the shifter mechanism 19, so as to insert the leading ends of a plurality of electrode pairs 17 into their corresponding wells 21 of the microplate 20 (step S32: position control step). Next, the data analyzer 50 determines an analysis region in a two-dimensional optical image included in moving image data to be processed (step S33: analysis region determination step).

Thereafter, the data analyzer 50 controls the position controller 30, so as to supply a voltage to the electrode pairs 17, thereby generating an electric field within the wells 21 of the microplate 20 (provision of electrical stimulation). In the state where the electric field is generated, the moving image acquisition unit 40 detects a two-dimensional optical image of the microplate 20 including fluorescence emitted from the sample S held within the wells 21, whereby the data analyzer 50 acquires moving image data representing the two-dimensional optical image. For the two-dimensional optical image included in the acquired moving image data, the data analyzer 50 analyzes the optical intensity in an analysis region which is set in a part of a region facing the electrode pairs 17 of the microplate 20 on the microplate holder 11, whereby analysis information concerning the sample S is obtained and outputted to the display device 61 (step S34: light detection step and information analysis step).

Figure 13:
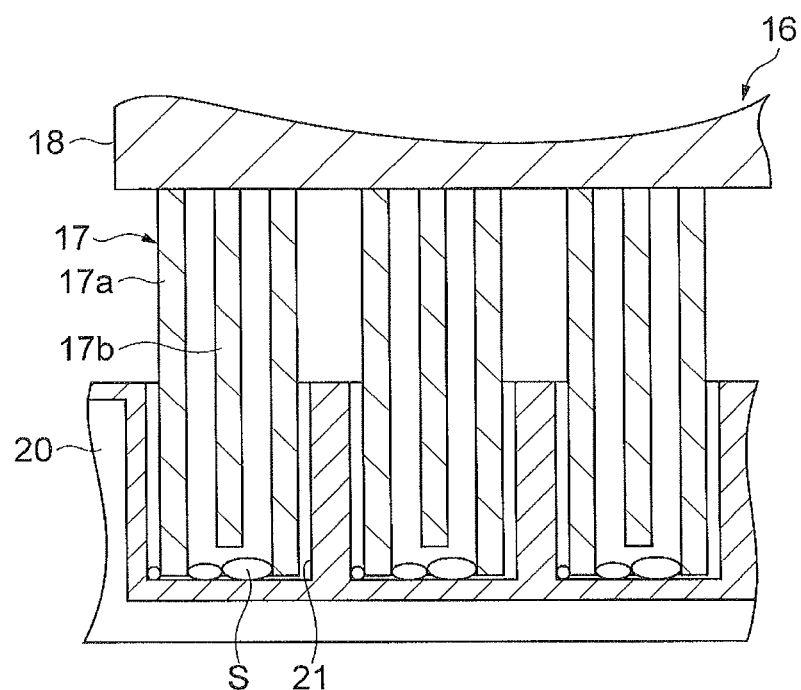
FIG. 13 is a partially broken sectional view illustrating a positional relationship between the electrical stimulator 16 and microplate 20 at the time of the operation for determining an analysis region.

Referring now to FIG. 12, the procedure of the analysis region determination step at the step S33 in FIG. 11 will be explained in detail. First, in a state where the microplate 20 for measurement is transferred to the measurement position P with the electrode pairs 17 being inserted into the wells 21 (FIG. 13), the excitation light source 43 irradiates the bottom face 22 of the microplate 20 (FIG. 3) with illumination light. Then, the moving image acquisition unit 40 detects a two-dimensional optical image of the microplate 20 including at least one well 21, and the data analyzer 50 acquires moving image data or still image data representing the two-dimensional optical image (step S41). Preferably, the two-dimensional optical image of the microplate 20 includes a plurality of wells 21. In this case, an analysis region can be set for a plurality of wells at once. Reflected images of the electrode pairs 17 are also projected on the two-dimensional optical image as a matter of course. At this time, the reflected image of the electrode pair 17 is based on the light reflected by the leading ends of the negative and positive electrodes 17a, 17b. For the two-dimensional optical image included in the acquired moving image data, the data analyzer 50 sets an analysis region in the two-dimensional optical image as in the steps S14, S15 in FIG. 6 (steps S42, S43). At this time, the data analyzer 50 sets the analysis region according to the reflected image of the leading end of the negative electrode 17a or positive electrode 17b of the electrode pair 17. Specifically, the form of the leading end of the negative electrode 17a or positive electrode 17b is identified from the two-dimensional optical image, and the analysis region is set according to this form.

Without being restricted to such an analysis region as to include a region where the leading end of the positive electrode 17b is extended onto the bottom face of the well 21 is set in the above-mentioned method for setting an analysis region by the cell observation system 1, the analysis region may be set as follows according to a threshold of electric field intensity to which the cell included in the sample S reacts and a threshold of electric field intensity at which the cell is damaged.

Figure 14:
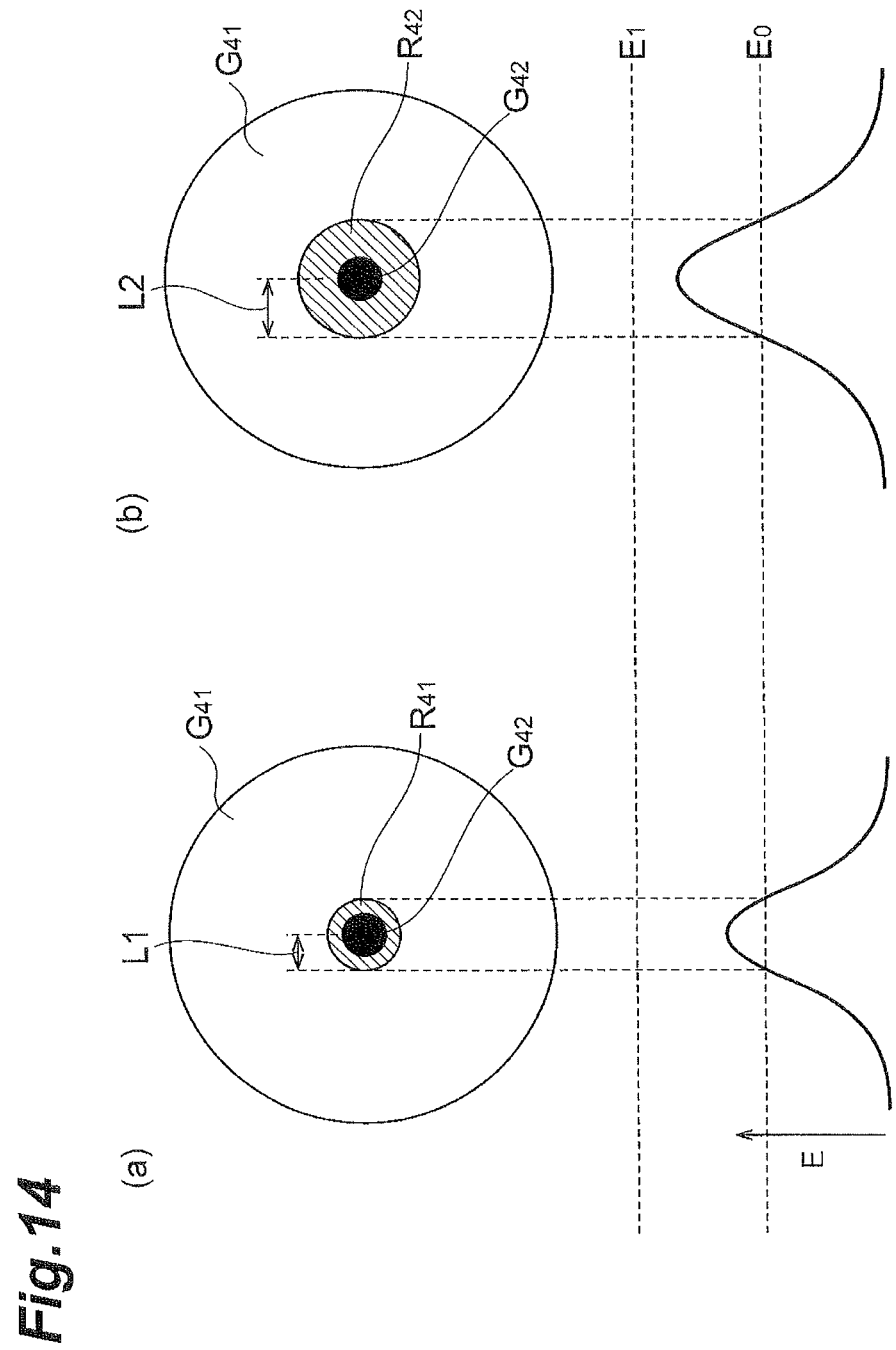
FIG. 14 is a diagram illustrating a range of an analysis region set in an image of a well 21 captured by a moving image acquisition unit 40.
Figure 15:
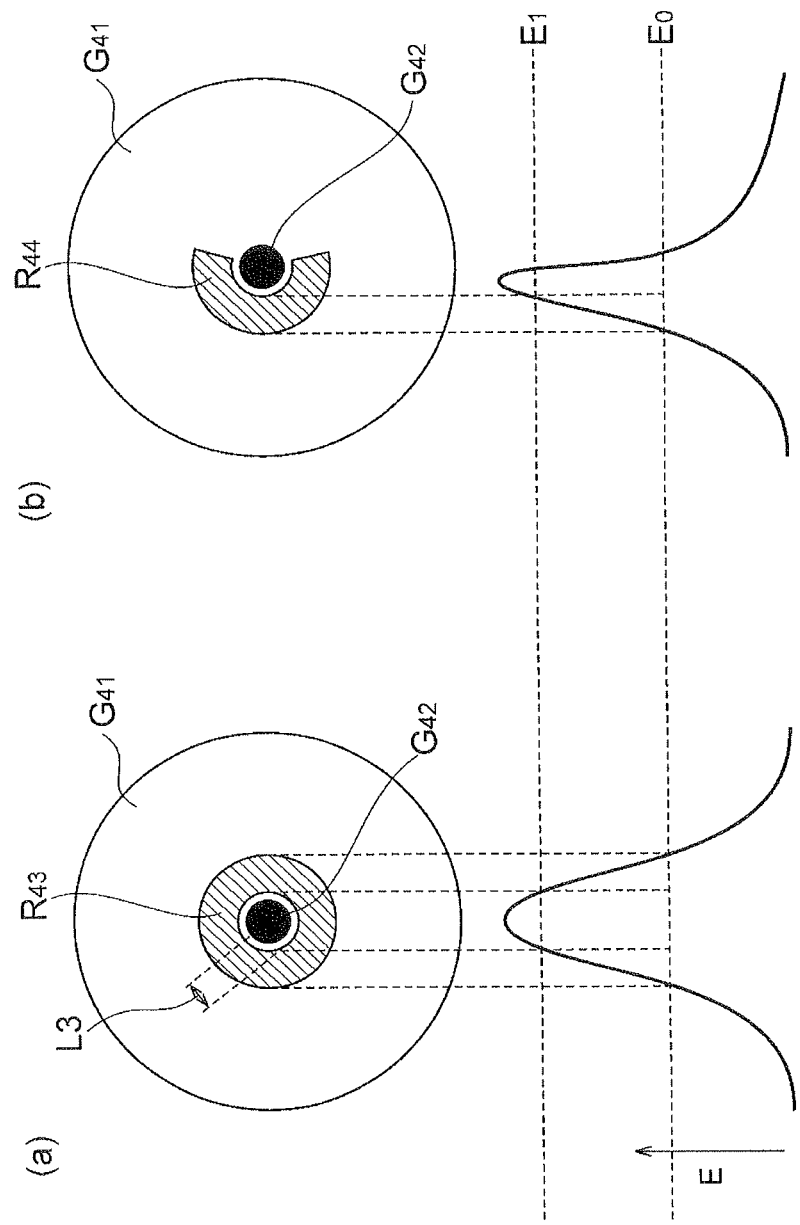
FIG. 15 is a diagram illustrating a range of an analysis region set in an image of the well 21 captured by the moving image acquisition unit 40.

FIGS. 14(a) and (b) and FIGS. 15(a) and (b) illustrate ranges of analysis regions set in images of the wells 21 captured by the moving image acquisition unit 40 and distributions of electric field intensity E within the wells 21 corresponding to the images.

FIG. 14(a) is an example of setting of the analysis region in a case where the potential applied to the electrode pair 17 is relatively low; a circular analysis region $R_{41}$ is set so as to cover a reflected image $G_{42}$ of the positive electrode 17b detected at the center of a reflected image $G_{41}$ of the well 21. The analysis region $R_{41}$ is set such that the electric field intensity within this range is a value between a threshold $E_0$ of electric field intensity to which the cell reacts and a threshold $E_1$ of electric field intensity at which the cell is damaged. For example, assuming d to be the distance from the leading end of the positive electrode 17b of the electrode pair 17 to the bottom face of the well 21, and a to be the radius of the reflected image $G_{42}$ of the positive electrode 17b, the analysis region $R_{41}$ is set to a circle having a radius L1 from the center of the reflected image $G_{42}$ as the range of a part on the well 21 facing the positive electrode 17b, while the radius L1 is set to a value within the range of $a \leq L1 \leq a+d$. When the reaction of the cell of the sample S is vigorous, the radius L1 may be set to a value within the range of $0<L1<a$.

FIG. 14(b) is an example of setting of the analysis region in a case where the potential applied to the electrode pair 17 is relatively high; a circular analysis region $R_{42}$, which is larger than the analysis region $R_{41}$, is set so as to cover the reflected image $G_{42}$ of the positive electrode 17b detected at the center of the reflected image $G_{41}$ of the well 21. The analysis region $R_{42}$ includes not only the region where the leading end of the positive electrode 17b is extended onto the bottom face of the well 21 but also a ring-shaped nearby region on the outside of the former region and is set such that the electric field intensity within this range is a value between the threshold $E_0$ of electric field intensity to which the cell reacts and the threshold $E_1$ of electric field intensity at which the cell is damaged. For example, assuming d to be the distance from the leading end of the positive electrode 17b of the electrode pair 17 to the bottom face of the well 21, and a to be the radius of the reflected image $G_{42}$ of the positive electrode 17b, the analysis region $R_{42}$ is set to a circle having a radius L2 from the center of the reflected image $G_{42}$, while the radius L2 is set to a value within the range of $a+d<L2 \leq a+3 \times d$.

FIG. 15(a) is an example of setting of the analysis region in a case where the potential applied to the electrode pair 17 is made further higher; a ring-shaped analysis region $R_{43}$ is set on the outside of the reflected image $G_{42}$ of the positive electrode 17b detected at the center of the reflected image $G_{41}$ of the well 21. This analysis region $R_{43}$ is a ring-shaped nearby region on the outside of the region where the leading end of the positive electrode 17b is extended onto the bottom face of the well 21, while being set such that the electric field intensity within this range is a value between the threshold $E_0$ of electric field intensity to which the cell reacts and the threshold $E_1$ of electric field intensity at which the cell is damaged. That is, the analysis region is set such as to exclude a region at the center of the well 21 where the cell has been damaged. For example, assuming d to be the distance from the leading end of the positive electrode 17b of the electrode pair 17 to the bottom face of the well 21, and a to be the radius of the reflected image $G_{42}$ of the positive electrode 17b, the analysis region $R_{43}$ is set such as to exclude a circular region having a radius L3 from a circular region centered at a position corresponding to the center of the reflected image $G_{42}$, while the radius L3 is set to a value within the range of $0<L3 \leq a$.

FIG. 15(b) is an example of setting of the analysis region in a case where the potential applied by the electrode pair 17 is asymmetrical; a partially cut-out ring-shaped analysis region $R_{44}$ is set on the outside of the reflected image $G_{42}$ of the positive electrode 17b. The analysis region $R_{44}$ is set such that the electric field intensity within this range is a value between the threshold $E_0$ of electric field intensity to which the cell reacts and the threshold $E_1$ of electric field intensity at which the cell is damaged. That is, such an analysis region is set as to exclude a part where the electric field intensity is so low that the cell is less reactive on the outside of the reflected image $G_{42}$ of the positive electrode 17b.

In the cell observation system 1 and cell observation method by the cell observation system 1 explained in the foregoing, the electrode pairs 17 including the positive and negative electrodes 17b, 17a are placed in a plurality of wells 21 arranged in the microplate 20, and fluorescence from the sample S within the wells 21 is detected by the moving image acquisition unit 40 in a state where an electric field is generated by the electrode pairs 17, and the data analyzer 50 sets a part of the region facing the positive electrode 17b on the well 21 as an analysis region for a two-dimensional optical image corresponding to a result of the detection, whereby analysis information is acquired according to the optical intensity of the analysis region. Hence, a range including the cell having generated a reaction to electrical stimulation is analyzed efficiently, whereby the ratio of the optical intensity caused by the reaction to the electrical stimulation to the optical intensity caused by noise can be increased. As a result, fluorescence from the sample S including a cell can be analyzed highly sensitively. When cells seeded on the microplate 20 are to be observed, it is difficult for the cells to be placed uniformly on the wells 21 in particular. The cell observation system 1 can optimize a detection region, so as to yield highly sensitive analysis results.

The above-mentioned cell observation system 1 sets such an analysis region as to include a region where the leading end of the positive electrode 17b is extended onto the bottom face of the well 21, so that a region where the applied electric field has a high intensity on the well 21 can be set as the analysis region, whereby the fluorescence from the sample S can be analyzed with a higher sensitivity.

By setting such an analysis region as to include the region where the leading end of the positive electrode 17b is extended and its nearby region, a region where the applied electric field has a high intensity on the well 21 can widely be set as an analysis region even when the cell is relatively less reactive on the well 21, whereby the fluorescence from the sample S can be analyzed with a higher sensitivity.

By setting such an analysis region as to include a region which is near the region where the leading end of the positive electrode 17b is extended but excludes the latter region, a range of the cell having produced a reaction can efficiently be set as an analysis region even when the applied electric field is so strong on the well 21 that the cell is damaged. That is, the extended region of the leading end of the positive electrode 17b, where the electrodes come into contact with the cell or the electric field is so strong that the cell is not reactive, is excluded from the analysis, while the vicinity of the extended region is set as the analysis region since the cell is easy to react there. This can yield analysis results with less noise for the cell that has produced the reaction.

The present invention is not limited to the above-mentioned embodiment. For example, the data analyzer 50 may set the analysis region as follows so as to change the size of the analysis region according to the potential supplied to the electrode pair 17. Suppose a case where the applied voltage is raised from $E_2$ to $E_3=n\times E_2$ (where n is an integer of 2 or greater) after setting the analysis region $R_{41}$ having the radius L1 as illustrated in FIG. 14(a). In this case, letting G be the distance between an edge of the reflected image $G_{42}$ of the positive electrode 17b and an edge of the reflected image $G_{41}$ of the well 21, the analysis region $R_{42}$ having a radius L2=a+L4 is set as illustrated in FIG. 14(b), and the added value L4 to the radius at this time is set to a value $L4=(1-1/n)\times G$ which is enhanced as the multiplying factor for the applied voltage increases.

The structure of the electrode pair 17 in the electrical stimulator 16 is not limited to the coaxial form but can employ various forms. The data analyzer 50 can set the analysis region according to the structure of the electrode pair 17.

As mentioned above, the data analyzer 50 sets an analysis region for the well 21 according to a two-dimensional optical image of the microplate 20 mounted on the microplate holder 11. Here, the data analyzer 50 may be configured so as to set the analysis region according to a reflected image of a subject included in the two-dimensional optical image of the microplate 20. In this case, the subject is not limited to but may be the inner wall of the well 21 of the microplate 20 or the negative electrode 17a or positive electrode 17b of the electrical stimulator 16. Analysis regions can appropriately be set for a plurality of wells in these cases.

Figure 16:
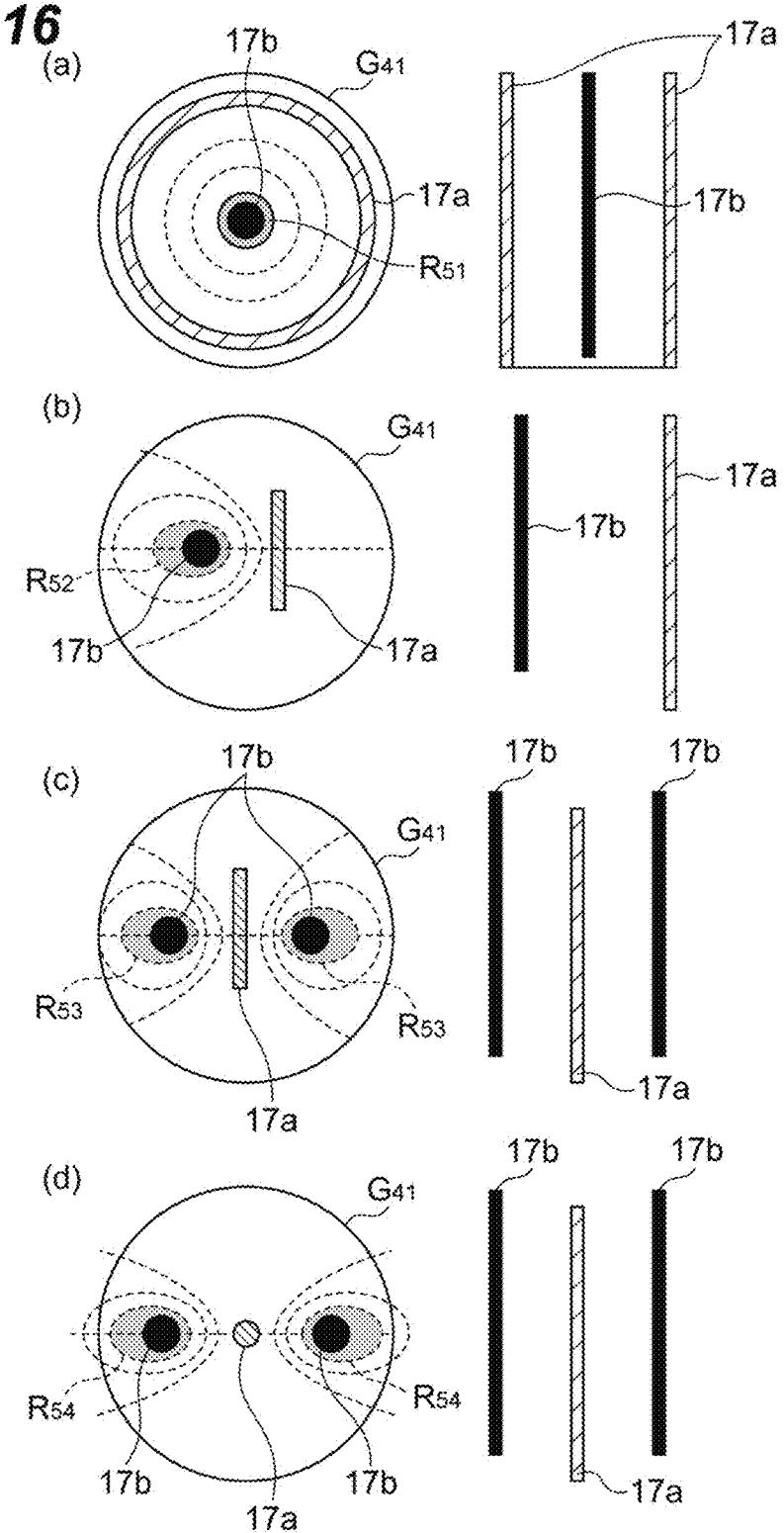
FIG. 16 is a diagram illustrating structures of electrode pairs 17 in accordance with modified examples of the embodiment and images of analysis regions set correspondingly thereto by the data analyzer 50.

FIGS. 16 and 17 illustrate structures of electrode pairs 17 in accordance with modified examples of the embodiment and images of analysis regions set correspondingly thereto by the data analyzer 50. Each of FIGS. 16(a) to (d) and FIGS. 17(a) and (b) illustrates cross sections of the electrode pair 17 taken perpendicularly to and along the bottom face of the microplate 20 on the right and left sides, respectively, together with ranges of analysis regions $R_{51}$ to $R_{56}$ set on the inside of the reflected image $G_{41}$ of the well 21. Dotted lines within the reflected image $G_{41}$ illustrate equipotential lines of the potential formed by the electrode pair 17. As these diagrams represent, the electrode pair 17 can employ not only the coaxial form illustrated in FIG. 16(a), but also a structure of a combination of a rod-shaped positive electrode 17b and a planar negative electrode 17a as illustrated in FIG. 16(b), a structure in which two rod-shaped positive electrodes 17b face each other across a planar negative electrode 17a as illustrated in FIG. 16(c), a structure in which two rod-shaped positive electrodes 17b face each other across a rod-shaped negative electrode 17a as illustrated in FIG. 16(d), a structure of a combination of a rod-shaped positive electrode 17b and a rod-shaped negative electrode 17a as illustrated in FIG. 17(a), and a combination of a rod-shaped positive electrode 17b and two rod-shaped negative electrodes 17a opposing to it as illustrated in FIG. 17(b). A structure of a parallel electrode pair in which planar positive and negative electrodes are placed in parallel may also be employed. Each of the ranges of the analysis regions $R_{51}$ to $R_{56}$ for the structures of electrode pairs 17 is set to a range which is a part of a region facing the leading end of the positive electrode 17b on the bottom face of the microplate 20, including a range where the leading end of the positive electrode 17b is extended, and corresponding to the form of an equipotential line near the leading end of the positive electrode 17b.

Though the above-mentioned embodiment is configured such that the microplate 20 to be measured holding the sample S within the microplate stocker 13 is transferred by the microplate transfer mechanism 12 to the measurement position P within the dark box 15 while being mounted on the microplate holder 11, a structure in which the microplate 20 is manually placed at the measurement position P within the dark box 15 may also be employed.

In the cell observation system 1 and cell observation method by the cell observation system 1 in the above-mentioned embodiment, myocardial cells (cells constituting cardiac muscles) and skeletal muscle cells constituting muscles may be used as the sample S to be measured. The myocardial cells and skeletal muscle cells expand and contract as triggered by action potentials. Here, since calcium ions migrate through a cell membrane from the outside to inside of a cell or vice versa, dyeing calcium ions with a pigment reactive thereto and observing its fluorescence can show how the myocardial cells and skeletal muscle cells expand and contract. While muscle cells within organisms typically expand and contract with the aid of pacemaker cells which control action potentials, myocardial cells and skeletal muscle cells produced from stem cells such as iPS cells and ES cells may lack cells to become a pacemaker or fail to be controlled well. Even such muscle cells can be expanded and contracted when electrical stimulation is imparted thereto from the outside by using the cell observation system 1 so as to control action potentials. There have recently been increasing demands for evaluating drug discovery by using myocardial cells and skeletal muscle cells. In particular, this embodiment performing electrical stimulation from the outside is effective as a technique for evaluating various chemical compounds, since it not only enables usual pacing but also makes it possible to evaluate compounds whose efficacy depends on the beating rate and intentionally cause arrhythmia.

An example using a muscle cell as a subject will now be explained.

Employed as the sample S held within 96 wells 21 of the microplate 20 is one in which a myocardial cell of a heart (ventricle) of a 1-to-4-day-old SD rat was cultivated to $2 \times 10^4$ cells per well. Used as the microplate 20 was one in which the wells 21 were coated with collagen I. The myocardial cell was dyed with a calcium dye (Cal520-AM).

At the position control step (FIG. 5: S03), the data analyzer 50 controls the electrode pairs 17 so that they are placed within the wells 21 holding the myocardial cells. At the light detection step (FIG. 5: S04) thereafter, a voltage is applied to the electrode pairs 17 under the control of the data analyzer 50, so as to impart electrical stimulation to the myocardial cells within the wells 21. Specifically, a pulse voltage in the form of a rectangular wave having a peak value of 5 V and a time width of 5 ms is applied for 5 sec at a repetition frequency of 1 Hz. The repetition frequency is preferably set within the range of 0.5 Hz to 2 Hz. At the same time, the data analyzer 50 acquires moving image data representing a two-dimensional optical image of the microplate 20 for 31 ms per frame, i.e., at a frame rate of 30 frames/sec, while the voltage is applied to the electrode pairs 17. Then, the data analyzer 50 analyzes fluorescence intensity in the analysis region by using the acquired moving image data.

Figure 18:
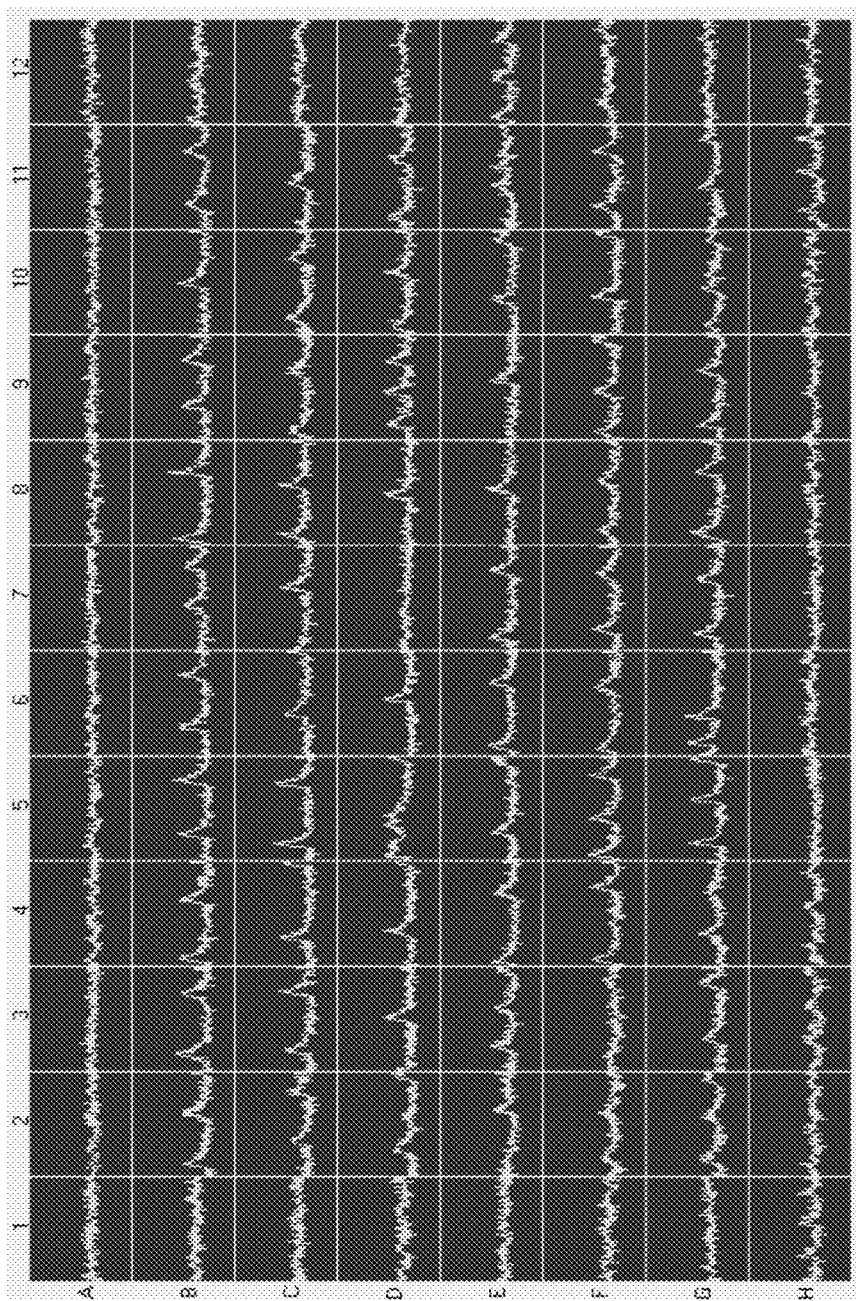
FIG. 18 is a chart illustrating results of measurement of changes with time of average fluorescence intensities in respective analysis regions for two-dimensional optical images in 96 wells 21 acquired when no electrical stimulation was performed in the cell observation system 1.
Figure 19:
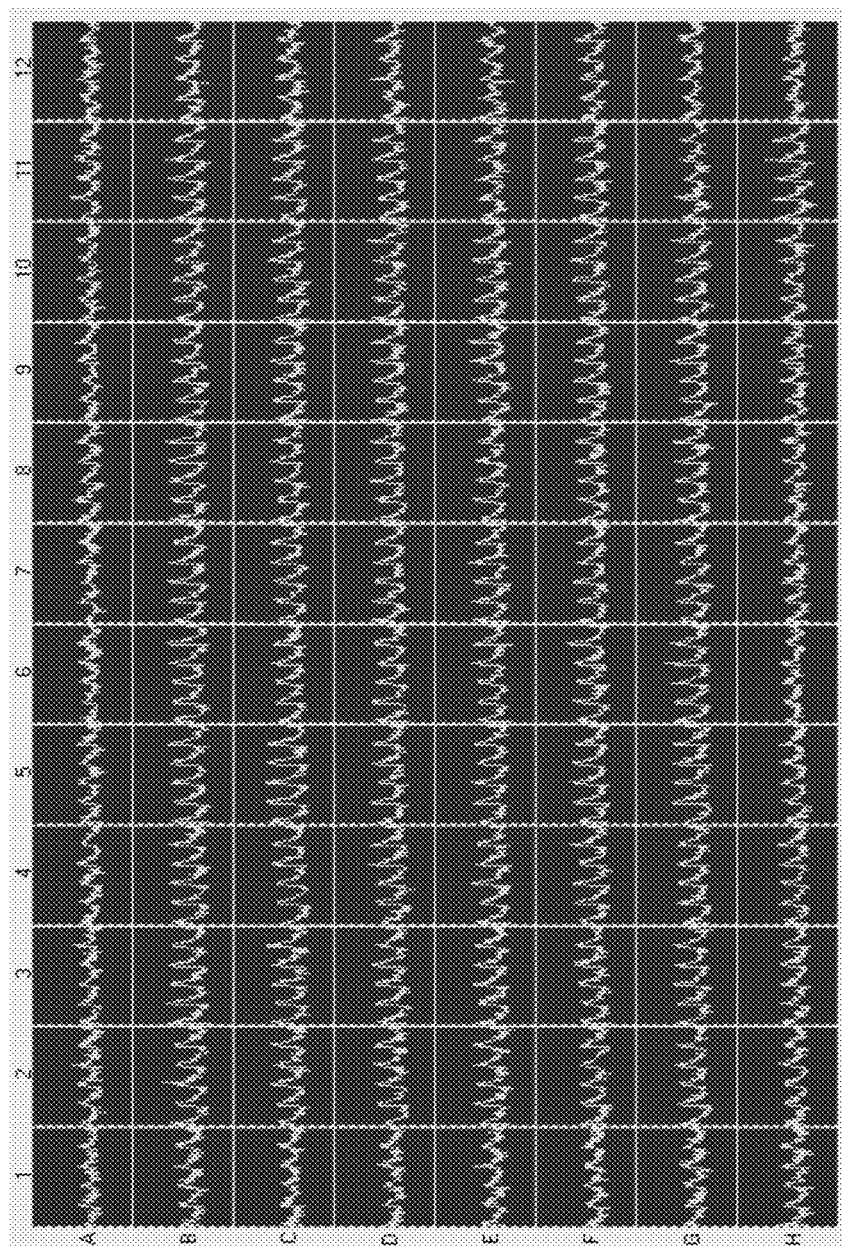
FIG. 19 is a chart illustrating results of measurement of changes with time of average fluorescence intensities in respective analysis regions for two-dimensional optical images in 96 wells 21 acquired when electrical stimulation was performed in the cell observation system 1.

FIGS. 18 and 19 illustrate measurement results of changes with time of average fluorescence intensity in the analysis region of the two-dimensional optical image in each of 96 wells 21 acquired in this example without and with the electrical stimulation by the pulse voltage, respectively. The measurement results for the respective wells 21 are arranged two-dimensionally in columns 1 to 12 and lines A to H. It is seen from the measurement results that, when no pacing with the pulse voltage is performed, cells to become a pacemaker appear to act in a part of the 96 wells so as to change the fluorescence intensity, but there are wells where pacemakers do not work at all. When pacing with the pulse voltage is performed, on the other hand, changes in fluorescence intensity are observed in all of the 96 wells.

Figure 20:
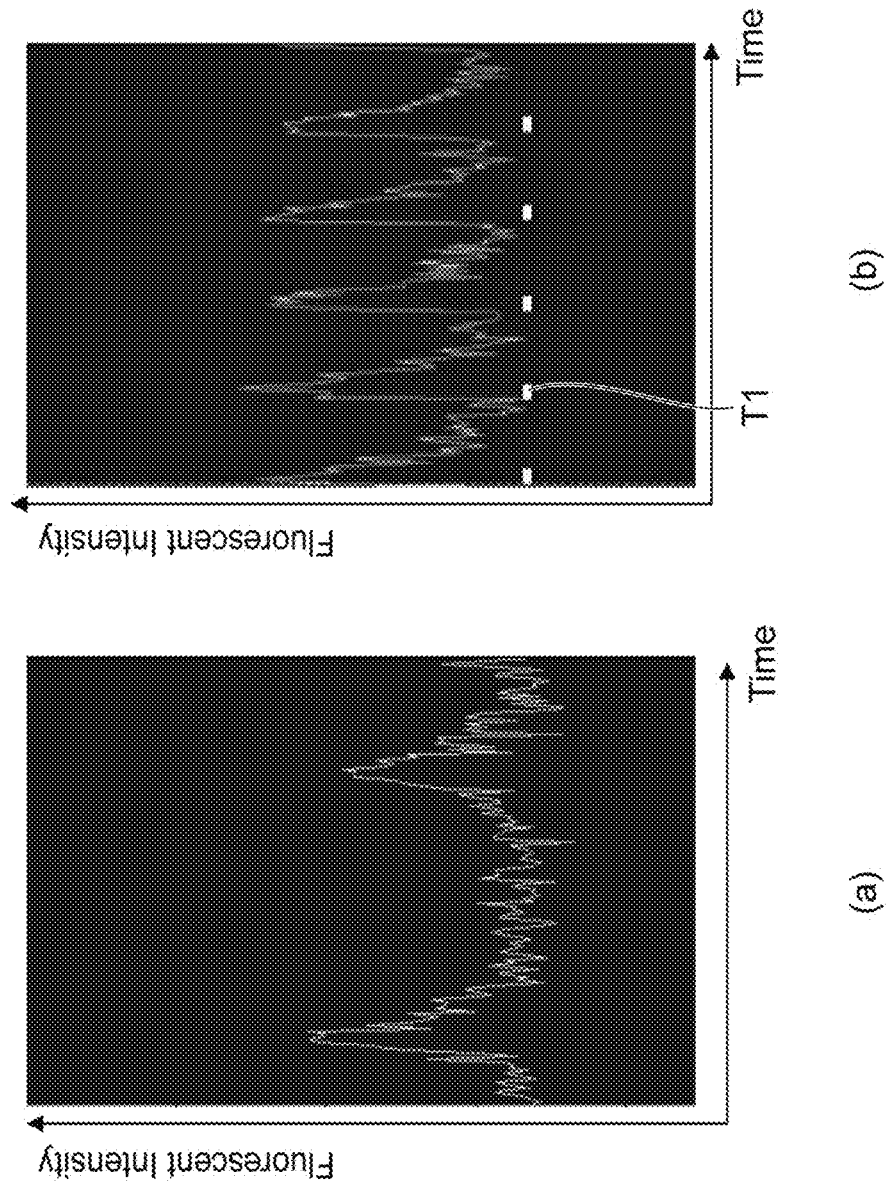
FIG. 20 is a chart illustrating results of measurement corresponding to one well as extracted from the results of measurement in FIGS. 18 and 19.

FIG. 20 illustrates the measurement results of the well at column 3, line B as extracted from those in FIGS. 18 and 19, in which (a) and (b) show the results without and with the electrical stimulation, respectively. Thus, while irregular peaks are observed without pacing, periodical fluorescence peaks are seen in response to timings T1 of electrical stimulation when pacing is performed, which verifies that the above-mentioned cell observation system and cell observation method are effective for pacing myocardial cells.

By randomly applying a rectangular-wave pulse voltage to myocardial cells, the above-mentioned cell observation system and cell observation method are effective in observation in an arrhythmic state.

Preferably, in the above-mentioned cell observation system, the information analysis unit sets the analysis region according to a reflected optical image of a subject in the optical intensity distribution. Preferably, in the above-mentioned cell observation system, the information analysis step sets the analysis region according to a reflected optical image of a subject in the optical intensity distribution. This can easily specify the region facing the positive electrode on the holding unit, whereby the analysis region can be set efficiently and accurately.

Preferably, the subject is a leading end of the negative or positive electrode in the electrical stimulator. In this case, the analysis region can be set more accurately.

Preferably, the subject is an inner wall of the holding unit of the sample case. This enables the analysis region to be set more securely.

Preferably, the information analysis unit sets the analysis region so as to include a region where the leading end of the positive electrode is extended. This structure makes it possible to set a region where the applied electric field has a high intensity on the holding unit as the analysis region, whereby light from the sample can be analyzed with a higher sensitivity.

Preferably, the information analysis unit sets the analysis region so as to include a region where the leading end of the positive electrode is extended and a nearby region thereof. Providing this information analysis unit makes it possible to set a region where the applied electric field has a high intensity on the holding unit widely as the analysis region even when the cell is relatively less reactive on the holding unit, whereby the fluorescence from the sample can be analyzed with a higher sensitivity.

Preferably, the information analysis unit sets the analysis region so as to include a region near a region where the leading end of the positive electrode is extended but exclude the latter region. Providing this information analysis unit makes it possible to set a range of a cell having produced a reaction even when the applied electric field is so strong on the holding unit that the cell is damaged.

INDUSTRIAL APPLICABILITY

The present invention is used for a cell observation system and a cell observation method which measure light emitted from a sample including a cell when a voltage is applied thereto and can highly sensitively analyze light from the sample within a plurality of arranged holding units.

REFERENCE SIGNS LIST

1: cell observation system; 11: microplate holder (mounting unit); 16: electrical stimulator; 17: electrode pair; 17a: negative electrode; 17b: positive electrode; 20: microplate (sample case); 21: well (holding unit); 22: bottom face; 30: position controller (position control unit); 40: moving image acquisition unit (light detection unit); 50: data analyzer (information analysis unit); S: sample.

The invention claimed is:

1. A system for measuring light emitted from a cell held by a sample case comprising an inner holder that holds a sample including the cell, the system comprising:
a holder configured to hold the sample case;
an electrical stimulator comprising electrode pair comprising a first electrode and a second electrode;
a position controller configured to control a position of the electrical stimulator so as to place the electrode pair within the inner holder of the sample case;
a light detector comprising a two-dimensional pixel structure and configured to detect light from the sample within the inner holder of the sample case; and
an information analyzer coupling the light detector and configured to set a part of a region facing the first electrode on the inner holder as an analysis region for an optical intensity distribution obtained according to a result of detection by the light detector and analyze an optical intensity in the analysis region so as to acquire analysis information concerning the sample.

2. The system according to claim 1, wherein the information analyzer sets the analysis region according to a reflected optical image of a subject in the optical intensity distribution.

3. The system according to claim 2, wherein the subject comprises a leading end of the second electrode or first electrode in the electrical stimulator.

4. The system according to claim 2, wherein the subject comprises an inner wall of the holding unit of the sample case.

5. The system according to claim 1, wherein the information analyzer sets the analysis region so as to include a region where a leading end of the first electrode is extended.

6. The system according to claim 1, wherein the the analysis region comprises a circle having a radius, L2, wherein the radius is based upon the following:

$$a+d<L2\leq a+3\times d$$

wherein a distance, d, corresponds to a leading edge of the first electrode of the electrode pair to the bottom face of the container, and a is a radius of the reflected image.

7. The system according to claim 1, wherein the system is configured to define the analysis region to exclude a circular region having a radius, L3, centered at a position corresponding to an extended region of the first electrode, wherein the radius L3 is based upon the following:

$$0<L3\leq a$$

wherein a is a radius of the extended region.

8. The system according to claim 1, wherein the position controller performs such control as to place the electrode pair within the holding unit; and wherein the information analyzer analyzes the optical intensity of the analysis region in a state where a pulse voltage is repeatedly applied to the electrode pair.

9. A method for measuring light emitted from a cell held by a sample case comprising an inner holder that holds a sample including the cell, the method comprising:

holding the sample case by a holder;

controlling a position of an electrical stimulator comprising electrode pair comprising a first electrode and a second electrode so as to place the electrode pair within the inner holder of the sample case;

detecting light from the sample within the inner holder of the sample case by a light detector;

setting a part of a region facing the first electrode on the inner holder as an analysis region for an optical intensity distribution obtained according to a result of detection in the detecting; and analyzing an optical intensity in the analysis region so as to acquire analysis information concerning the sample.

10. The method according to claim 9, wherein the setting sets the analysis region according to a reflected optical image of a subject in the optical intensity distribution.

11. The method according to claim 10, wherein the subject comprises a leading end of the second electrode or first electrode in the electrical stimulator.

12. The method according to claim 10, wherein the subject comprises an inner wall of the holding unit of the sample case.

13. The method according to claim 9, wherein the controlling performs such control as to place the electrode pair within the holding unit; and wherein the analyzer analyzes the optical intensity of the analysis region in a state where a pulse voltage is repeatedly applied to the electrode pair.

* * * * *